United States Patent [19]

Bagli

[11] Patent Number: 4,505,910

[45] Date of Patent: Mar. 19, 1985

[54] AMINO-PYRIMIDINE DERIVATIVES, COMPOSITIONS AND USE

[75] Inventor: Jehan F. Bagli, Kirkland, Canada

[73] Assignee: American Home Products Corporation, New York, N.Y.

[21] Appl. No.: 509,886

[22] Filed: Jun. 30, 1983

[51] Int. Cl.$^3$ ............... A61K 31/505; A61K 31/535; C07D 239/47; C07D 413/12
[52] U.S. Cl. .................. 514/26; 424/248.5; 424/248.56; 424/249; 424/251; 544/58.6; 544/60; 544/105; 544/122; 544/123; 544/182; 544/209; 544/212; 544/238; 544/295; 544/296; 544/319; 544/326; 544/327; 544/328; 544/279; 514/222; 514/229; 514/237; 514/241; 514/252; 514/256; 514/228; 514/234; 514/238; 514/248; 514/269; 514/254
[58] Field of Search ............... 544/58.6, 60, 105, 122, 544/123, 238, 209, 212, 182, 295, 296, 319, 326, 327, 328, 279; 424/246, 248.5, 248.56, 249, 251

[56] References Cited

U.S. PATENT DOCUMENTS 4,072,746  2/1978  Lesher et al. ............... 424/263
4,313,951  2/1982  Lesher et al. ............... 424/263

FOREIGN PATENT DOCUMENTS 2410650  9/1975  Fed. Rep. of Germany .
  72790  5/1970  German Democratic Rep. .
 101894 11/1973  German Democratic Rep. .
7108698  3/1971  Japan .
7176981 10/1982  Japan .
7210637  2/1973  Netherlands .
1189188 11/1966  United Kingdom .

OTHER PUBLICATIONS

S. Kisaki et al., Chem. Pharm. Bull., 22, 2246, (1974).
A. Kumar et al., Synthesis, (9), 748, (1980).

*Primary Examiner*—Robert W. Ramsuer

[57] ABSTRACT

Herein is disclosed amino-pyrimidine derivatives, therapeutically acceptable acid addition salts thereof, processes for their preparation, methods of using the derivatives and pharmaceutical compositions. The derivatives are useful for increasing cardiac contractility in a mammal.

33 Claims, No Drawings

AMINO-PYRIMIDINE DERIVATIVES, COMPOSITIONS AND USE

BACKGROUND OF THE INVENTION

This invention relates to novel amino-pyrimidine derivatives, to therapeutically acceptable addition salts thereof, to processes for their preparation, to methods of using the derivatives and to pharmaceutical compositions of the derivatives. These derivatives are useful as cardiotonic agents for increasing cardiac contractility.

Related hereto is my patent application Ser. No. (AHP-8318) filed on even date herewith.

Although the amino-pyrimidine derivatives of this invention are novel compounds, a number of pyrimidines and 4-oxopyrimidines are described, for example, B. Rogge et al., Chem. Abstr. 81, 25691m (1974) for East German Pat. No. 101,894, Nov. 20, 1973; S. Kisaki et al., Chem. Pharm. Bull., 22, 2246 (1974); Derwent Publications Ltd., Farmdoc 62457W for German Offenlegenshift No. 2,410,650, published Sept. 11, 1975; Derwent Publications Ltd., Farmdoc 05783J for Japanese Pat. No. 7,176,981, published Oct. 10, 1982; Derwent Publications Ltd., Farmdoc 10368U for Netherland Pat. No. 7,210,637, published Feb. 6, 1973; Chemical Abstracts, 75, 49129m (1971) for Japanese Pat. No. 7,108,698, published Mar. 5, 1971; A. Kumar et al., Synthesis, (9), 748 (1980); Derwent Publications Ltd., Farmdoc 46076R for East German Pat. No. 72,790, published May 5, 1970; and Derwent Publications Ltd., Farmdoc 31812R for British Pat. No. 1,189,188, published Nov. 9, 1966. The pyrimidines described in the above reports are distinguished from the compounds of this invention by the different substituents on the pyrimidine ring and the reported biological activity. The amino-pyrimidine derivatives of this invention are also distinguished from the cardiotonic pyridinones, exemplified by G. Y. Lesher et al., U.S. Pat. No. 4,072,746, Feb. 7, 1978 and G. Y. Lesher et al., U.S. Pat. No. 4,313,951, Feb. 2, 1982, by having different rings and different substitution on the rings.

SUMMARY OF THE INVENTION

The compounds of this invention are represented by formula I

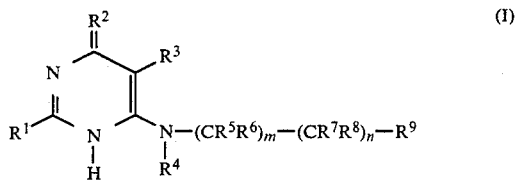

in which $R^1$ is lower alkyl, cyclo(lower)alkyl, phenyl(lower)alkyl, or trifluoromethyl; $R^2$ is oxo, thioxo, or imino; $R^3$ is cyano, aminocarbonyl, nitro, methylsulfonyl or aminosulfonyl; $R^4$, $R^5$, $R^6$, $R^7$ and $R^8$ each independently is hydrogen or lower alkyl; $R^9$ is lower alkenyl, 1-piperidinyl, 1-pyrrolidinyl, 1-piperazinyl, lower alkynyl, cyclo(lower)alkyl, 2, 3 or 4-pyridinyl, 2 or 3-furanyl, 2 or 3-indolyl, 2 or 3-thienyl, 5-imidazolyl, 4-morpholinyl, phenyl, phenyl mono- or disubstituted with hydroxy or lower alkoxy, imidazolyl, 4-thiomorpholinyl, pyrazinyl, pyridazinyl, triazinyl, pyrrolyl, pyrazolyl, thiazolyl, oxadiazolyl, thiadiazolyl, isoxazolyl, furazolyl, oxathiazolyl, quinolinyl, isoquinolinyl, pyridopyrimidinyl, benzoxazolyl, benzimidazolyl, benzthiazolyl, benzoxazinyl, benzpyronyl, isoindolyl, or indolazinyl; and m and n each independently is an integer 0 to 2; or a therapeutically acceptable addition salt thereof.

A preferred group of compounds of this invention is represented by formula I in which $R^1$ is lower alkyl, cyclo(lower)alkyl or benzyl; $R^2$ is oxo, thioxo or imino; $R^3$ is cyano or aminocarbonyl; $R^4$, $R^6$ and $R^8$ each independently is hydrogen or lower alkyl, $R^5$ and $R^7$ are hydrogen; $R^9$ is lower alkenyl, cyclo(lower)alkyl, 2, 3 or 4-pyridinyl, 2 or 3-furanyl, 2 or 3-indolyl, 2 or 3-thienyl, 4-morpholinyl, phenyl or phneyl mono- or disubstituted with hydroxy or lower alkoxy; and m and n each independently is an integer 0 to 2; or a therapeutically acceptable addition salt thereof.

A more preferred group of compounds of this invention is represented by formula I in which $R^1$ is lower alkyl, cyclo(lower)alkyl or benzyl; $R^2$ is oxo or thioxo; $R^3$ is cyano; $R^4$, $R^5$ and $R^7$ are hydrogen; $R^6$ and $R^8$ each independently is hydrogen or lower alkyl; $R^9$ is lower alkenyl, 2, 3 or 4-pyridinyl, 2-furanyl, 3-indolyl, 3-thienyl, 4-morpholinyl, phenyl or phenyl mono- or disubstituted with lower alkoxy; and m and n each independently is the integer 0 or 1; or a therapeutically acceptable addition salt thereof.

This invention also relates to a pharmaceutical composition comprising a compound of formula I or a therapeuticaly acceptable addition salt thereof and a pharmaceutically acceptable carrier.

This invention also relates to a method for increasing cardiac contractility in a mammal which comprises administering to the mammal an effective cardiotonic amount of a compound of formula I or a therapeutically acceptable addition salt thereof.

DETAILED DESCRIPTION OF THE INVENTION

The term "lower alkyl" as used herein means straight and branched chain alkyl radicals containing from one to six carbon atoms, preferably one to four carbon atoms, and includes methyl, ethyl, propyl, 1-methylethyl, butyl, 1,1-dimethylethyl, pentyl and the like, unless stated otherwise.

The term "lower alkenyl" as used herein means straight chain alkenyl radicals containing from two to six carbon atoms and branched chain alkenyl radicals containing three to six carbon atoms and includes ethenyl, 2-methyl-2-propenyl, 4-hexenyl and the like.

The term "lower alkynyl" as used herein means straight chain alkynyl radicals containing from two to six carbon atoms and branched chain alkynyl radicals containing four to six carbon atoms and includes ethynyl, 2-propynyl, 1-methyl-2-propynyl, 3-hexynyl and the like.

The term "cyclo(lower)alkyl" as used herein means saturated cyclic hydrocarbon radicals containing from three to six carbon atoms and includes cyclopropyl, cyclobutyl, cyclopentyl and cyclohexyl.

The term "lower alkanol" as used herein means both straight and branched chain alkanols containing from one to four carbon atoms and includes methanol, ethanol, 1-methylethanol, butanol and the like.

The term "inorganic proton acceptor" as used herein means the inorganic bases, preferably the alkali methyl hydroxides, alkoxides, carbonates and bicarbonates, for example, sodium hydroxide, potassium hydroxide, sodium carbonate, sodium bicarbonate, potassium carbonate, sodium hydride, sodium methoxide and the like.

The compounds of this invention are capable of forming acid addition salts with therapeutically acceptable acids. The acid addition salts are prepared by reacting the base form of the appropriate compound of formula I with one or more equivalents, preferably with an excess, of the appropriate acid in an organic solvent, for example, diethyl ether or an ethanoldiethyl ether mixture.

These salts, when administered to a mammal, possess the same pharmacologic activities as the corresponding bases. For many purposes it is preferable to administer the salts rather than the basic compounds. Suitable acids to form these salts include the common mineral acids, e.g. hydrohalic, sulfuric or phosphoric acid; the organic acids, e.g. maleic, citric or tartaric acid; and acids which are sparingly soluble in body fluids and which impart slow-release properties to their respective salts, e.g. pamoic or tannic acid or carboxymethyl cellulose. The addition salts thus obtained are the functional equivalent of the parent base compound in respect to their therapeutic use. Hence, these addition salts are included within the scope of this invention and are limited only by the requirement that the acids employed in forming the salts be therapeutically acceptable.

The compounds of formula I in which $R^2$ is oxo or thioxo are also capable of forming addition salts with sodium or potassium. These salts are prepared by reacting the latter compounds of formula I with one or more equivalents of sodium or potassium, or a strong base of sodium or potassium, for example, sodium hydroxide, potassium t-butoxide, sodium hydride and the like. These salts, like the acid addition salts, when administered to a mammal possess the same pharmacological activities as the corresponding nonsalt compound of formula I.

The compounds of formula I or a therapeutically acceptable addition salt thereof are useful as cardiotonic agents for increasing cardiac contractility in a mammal. The cardiotonic effect is demonstrated in standard pharmacological tests, for example, in causing an increase in the contractile force of the isolated cat papillary muscle and reversal of pentobarbital-induced cardiac failure in the dog.

The compounds of formula I of this invention are used alone or in combination with pharmacologically acceptable carriers, the proportion of which is determined by the solubility and chemical nature of the compound, chosen route of administration and standard biological practice. For example, they are administered orally in the form of suspensions or solutions or they may be injected parenterally. For parenteral administration they can be used in the form of a sterile solution containing other solutes, for example, enough saline or glucose to make the solution isotonic.

The tablet compositions contain the active ingredient in admixture with non-toxic pharmaceutical excipients known to be suitable in the manufacture of tablets. Suitable pharmaceutical excipients are, for example, starch, milk sugar, certain types of clay and so forth. The tablets can be uncoated or they can be coated by known techniques so as to delay disintegration and absorption in the gastrointestinal tract and thereby provide a sustained action over a longer period.

The aqueous suspensions of the compounds of formula I contain the active ingredient in admixture with one or more non-toxic pharmaceutical excipients known to be suitable in the manufacture of aqueous suspensions. Suitable excipients are, for example, methylcellulose, sodium alginate, gum acacia, lecithin and so forth. The aqueous suspensions can also contain one or more preservatives, one or more coloring agents, one or more flavoring agents and one or more sweetening agents.

Non-aqueous suspensions can be formulated by suspending the active ingredient in a vegetable oil, for example, arachis oil, olive oil, sesame oil, or coconut oil, or in a mineral oil, for example liquid paraffin, and the suspension may contain a thickening agent, for example, beeswax, hard paraffin or cetyl alcohol. These compositions can also contain a sweetening agent, flavoring agent and antioxidant.

The dosage of the compounds of formula I as cardiotonic agents will vary with the form of administration and the particular compound chosen. Furthermore, it will vary with the particular host as well as the age, weight and condition of the host under treatment as well as with the nature and extent of the symptoms. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side effects. For example, the effective cardiotonic amount of the compounds for oral administration can usually range from about 0.05 to 50 mg per kilogram body weight per day in single or divided doses although as aforementioned variations will occur. However, a dosage level that is in the range of from about 0.2 to 20 mg per kilogram body weight per day in single or divided doses is employed most desirably for oral administration in order to achieve effective results.

The compounds of formula I also can be used to produce beneficial effects in the treatment of congestive heart failure when combined with a therapeutically effective amount of another agent commonly used in the treatment of congestive heart failure. Such agents include, for example: vasodilators, i.e. isosorbide dinitrate, captopril, nifedipine, hydralazine and prazosin; diuretics, i.e. hydrochlorothiazide, furosemide and spironolactone; and other cardiotonics, i.e. digitalis and dobutamine. A combination of the above agents can be substituted for a single agent. Suitable methods of administration, compositions and dosages of the agents are well known in the art; for instance, "Physcan Desk Reference", 37 ed., Medical Economics Co., Oradell, N.J., U.S.A. 1983. When used in combination, the compound of formula I is administered as described previously.

The compounds of formula I are prepared in the following manner.

Reaction scheme 1 illustrates a method for preparing some of the compounds of formula I.

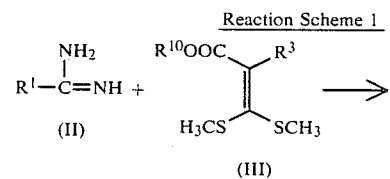

-continued
Reaction Scheme 1

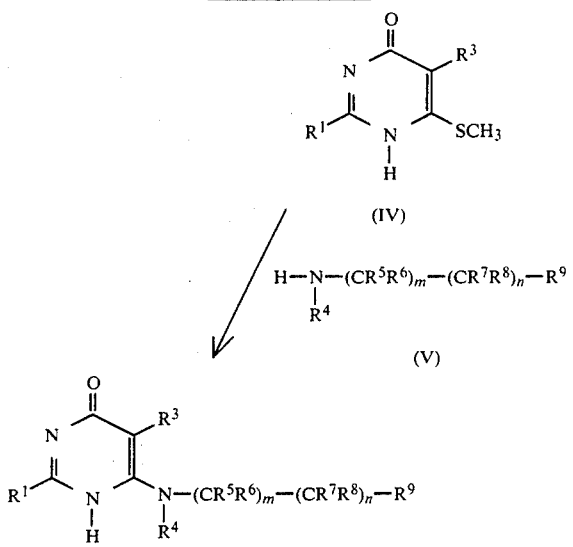

I in which $R^2$ is oxo and $R^3$ is cyano, nitro, methylsulfonyl or aminosulfonyl With reference to reaction scheme 1, the amidine of formula II in which $R^1$ is as defined herein is condensed with compound of formula III in which $R^3$ is cyano, nitro, methylsulfonyl or aminosulfonyl and $R^{10}$ is lower alkyl to obtain the pyrimidine of formula IV in which $R^1$ is as defined herein and $R^3$ is cyano, nitro, methylsulfonyl or aminosulfonyl according to the method described by S. Kisaki et al., Chem. Pharm. Bull., 22, 2246 (1974). This condensation is preferably achieved by reacting about equimolar amounts of the compounds of formulae II and III in the presence of an inorganic proton acceptor, for example, sodium hydride, sodium alkoxide or potassium carbonate, in an inert organic solvent, for example ethanol or dimethylformamide, at about 20° to 90° C. for about two to ten hours.

Reaction of the pyrimidine of formula IV in which $R^1$ is as defined herein and $R^3$ is cyano, nitro, methylsulfonyl or aminosulfonyl with the amine of formula V in which $R^4$ to $R^9$, m and n are as defined herein gives the corresponding compound of formula I in which $R^2$ is oxo, $R^3$ is cyano, nitro, methylsulfonyl or ainosulfonyl and $R^1$, $R^4$ to $R^9$, m and n are as defined herein. About one to five equivalents of the amine of formula V are usually used and the reaction is conducted in an inert organic solvent, preferably 1,2-dimethoxyethane, at about 50° to 100° C. for about 10 to 30 hours.

Reaction Scheme 2 illustrates another method for preparing some of the compounds of formula I Reaction Scheme 2

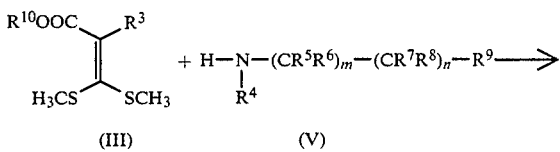

-continued
Reaction Scheme 2

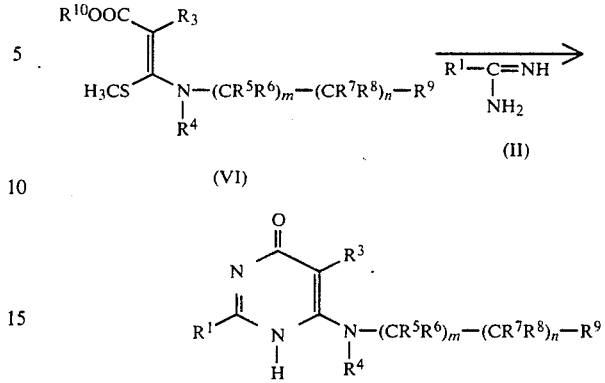

I in which $R^2$ is oxo and $R^3$ is cyano, nitro, methylsulfonyl or aminosulfonyl With reference to reaction scheme 2, the compound of formula III in which $R^3$ is cyano, nitro, methylsulfonyl or aminosulfonyl and $R^{10}$ is lower alkyl is reacted with the amine of formula V in which $R^4$ to $R^9$, m and n are as defined herein to obtain the corresponding compound of formula VI in which $R^3$ is cyano, nitro, methylsulfonyl or aminosulfonyl and $R^4$ to $R^{10}$, m and n are as defined herein. For this reaction, preferably about equimolar amounts of the compounds of formulae III and V are allowed to react at about 20° to 40° C. for about ten minutes to two hours in an inert organic solvent, preferably dimethoxyethane, and the compound of formula VI is isolated.

Condensation of the compound of formula VI in which $R^3$ is cyano, nitro, methylsulfonyl or aminosulfonyl and $R^4$ to $R^{10}$, m and n are as defined herein with the amidine of formula II in which $R^1$ is as defined herein gives the corresponding compound of formula I in which $R^2$ is oxo; $R^3$ is cyano, nitro, methylsulfonyl or aminosulfonyl; and $R^1$, $R^4$ to $R^9$, m and n are as defined herein. When conducting this condensation, preferably about equal molar amounts of the compounds of formula II and VI are condensed at about 75° to 150° C. for about 20 to 30 hours in an inert organic solvent, preferably dimethylformamide.

To convert the compound of formula I in which $R^2$ is oxo to the corresponding compound of formula I in which $R^2$ is thioxo, the following chemical reactions are required. In the first step, the sodium salt of the compound of formula I in which $R^2$ is oxo is reacted with an excess of phosphorous oxychloride at about 90° to 120° C. for about one to five hours to obtain the corresponding 4-chloropyrimidine derivative. Treatment of the latter derivative with a solution of water and ethanol containing an excess of potassium hydroxide and hydrogen sulphide at about 20° to 40° C. for about 20 to 30 hours gives the corresponding compound of formula I in which $R^2$ is thioxo; $R^3$ is cyano, nitro, methylsulfonyl or aminosulfonyl; and $R^1$, $R^4$ to $R^9$, m and n are as defined herein.

Treatment of the above 4-chloropyrimidine with a solution of an inert organic solvent, preferably a lower alkanol, containing an excess of ammonia at about 50° to 80° C. for about 20 to 30 hours gives the corresponding compound of formula I in which $R^2$ is imino; $R^3$ is cyano, nitro, methylsulfonyl or aminosulfonyl; and $R^1$, $R^4$ to $R^9$, m and n are as defined herein.

Hydrolysis of the compound of formula I in which $R^3$ is cyano; and $R^1$, $R^2$, $R^4$ to $R^9$, m and n are as defined herein, preferably with sulfuric acid at about 60° to 100° C. for one to ten hours, gives the corresponding compound of formula I in which $R^3$ is aminocarbonyl; and $R^1$, $R^2$, $R^4$ to $R^9$, m and n are as defined herein.

The following examples illustrate further this invention.

EXAMPLE 1

1,4-Dihydro-2-methyl-6-(methylthio)-4-oxo-5-pyrimidinecarbonitrile (IV: $R^1$=Me and $R^3$=cyano)

To a suspension of hexane washed sodium hydride (1.46 g, 50% in oil, 1.9 eq) in dimethylformamide (DMF, 1.5 mL) was added dropwise a solution of acetamidine hydrochloride (1.66 g, 1.1 eq) in DMF (7 mL). The reaction mixture was stirred at room temperature for 1 hr. A solution of 2-cyano-3, 3-bis(methylthio)-2-propenoic acid, methyl ester (described by R. Gompper et al., Chem. Ber., 95, 2861 (1962), 3.24 g, 1 eq) in DMF (5 mL, prepared by warming) was added dropwise. Some reaction occurred (evident by gas evolution) during addition. The reaction mixture was allowed to stir at room temperature for 4 hr and diluted with water (13 mL). After acidification with conc. hydrochloric acid (1.5 mL), the precipitate was collected and dried (2.2 g). This was combined with 2.8 g obtained from another such batch and crystallized from DMF (25 ml)/diethyl ether (30 mL), to yield the title compound (3.8 g): mp>280° C. and Anal. Calcd for $C_7H_7N_3OS$: C, 46.39% H, 3.89% N, 23.19% and Found: C, 46.39% H, 3.79% N, 23.27%.

EXAMPLE 2

1,4-Dihydro-2-methyl-4-oxo-6-[(3-pyridinylmethyl)amino]-5-pyrimidinecarbonitrile (I: $R^1$=Me, $R^2$=O, $R^3$=CN, $R^4$ to $R^8$=H, m=1, n=0 and $R^9$=3-pyridinyl)

To a solution of 1,4-dihydro-2-methyl-6-(methylthio)-4-oxo-5-pyrimidinecarbonitrile (described in Example 1, 1 eq, 4.4 g) in dimethoxyethane (33 mL) was added 3-aminomethylpyridine (9.87 mL or 10.53 g, 4 eq). The reaction mixture was refluxed for 18 hours. After about 2 hr of reflux the product started to precipitate. The reaction was cooled after 18 hr and diluted with methanol (12 mL), and the precipitate was filtered. The precipitate was washed with diethyl ether, and dried to yield white solid (5.97 g). A crystallization from hot dimethylformamide yielded the title compound: mp22 260° C.; Anal. Calcd for $C_{12}H_{11}H_5O$: C, 59.74% H, 4.60% N, 29.03% and found: C, 59.41% H, 4.75% N, 29.08%; IR (mineral oil) 3320, 2800, 2210, 1660 cm$^{-1}$; UV max (MeOH) 289 nm ($\epsilon$7250); 268 (8300); 263 (8200); 226 (40800); NMR (DMSO-d$_6$)$\delta$ 12.2 (1H, b), 8.5 (1H, b), 8.45 (2H, m), 7.5 (2H, m), 4.6 (2H, d), 2.25 (3H, s).

A suspension of the title compound (0.120 g, 1 eq) in methanol (1 mL), was stirred with methanolic hydrogen chloride (2N, 1 mL, 4 eq) added to it. The reaction mixture was stirred for 1.5 hr, diluted with diethyl ether (5 mL), and filtered. The solid was washed with diethyl ether, to yield crude product (0.16 g). Crystallization from methanol-water yielded the hydrochloride salt of the title compound (0.1 g): mp>250°; and Anal. Calcd for $C_{12}H_{11}N_5O.HCl$: C, 51.89% H, 4.32% N, 25.22% and Found: C, 51.81% H, 4.38% N, 25.18%.

To a stirred suspension of the title compound (0.491 g, 1 eq) in methanol (2 mL), was added a solution of sodium in methanol (2N, 1.99 mL, 1 eq). The solid went into solution over a period of 0.5 hr. The mixture was stirred overnight during which time some precipitate appeared. Diethyl ether (3 mL) was added, and the sodium salt (0.58 g) was filtered. One crystallization from methanol-diethyl ether yielded the sodium salt of the title compound (0.44 g): IR (mineral oil) 3660, 3630, 3420, 3320, 2850 cm$^{-1}$; and UV max (MeOH) 289 nm ($\epsilon$6680), 267 (7670), 263 (7570), 226 (38050).

In the same manner, but replacing 3-aminomethylpyridine with an equivalent amount of 3-N-methylaminomethylpyridine, 2-phenylethylamine, 2-(2-pyridinyl)ethylamine, 4-aminomethylpyridine, 2-aminomethylpyridine, benzylamine, 2-aminomethylfuran, N-(2-aminoethyl)morpholine, cyclohexanemethylamine, 3-(2-aminoethyl)thiophene, 2-(3,4-dimethoxyphenyl)ethylamine, 3-(2-aminoethyl)indole, (3-pyridinyl)ethylamine, (4-pyridinyl)ethylamine, the following compounds of formula I were obtained, respectively: 1,4-dihydro-2-methyl-6-[N-methyl-N-(3-pyridinylmethyl)amino]-4-oxo-5-pyrimidinecarbonitrile: mp 256°–258° C. (cryst. from methanol); IR (mineral oil) 2900, 2200, 1645 cm$^{-1}$; UV max (MeOH) 291 nm ($\epsilon$8490), 269 (9510), 263 (8950), 234 (32200); NMR (DMSO-d$_6$) $\delta$ 11.4 (br, 1H), 8.0 (m, 4H), 4.95 (s, 2H), 3.25 (s, 3H), 2.2 (s, 3H); Anal. Calcd for $C_{13}H_{13}N_5O$: C, 61.16% H, 5.13% N, 27.44% and Found: C, 60.84% H, 5.15% N, 27.37%; 1,4-dihydro-2-methyl-4-oxo-6-[(phenylethyl)amino]-5-pyrimidinecarbonitrile: mp 264°–266° C. (cryst. from methanol); NMR (DMSO-d$_6$) $\delta$ 12.0 (br, 1H), 7.8 (t, 1H), 7.2 (m, 5H), 3.55 (m, 2H), 2.8 (t, 2H), 2.2 (s, 3H); Anal. Calcd for $C_{14}H_{14}N_4O$: C, 66.12% H, 5.55% N, 22.03% and Found: C, 66.11% H, 5.60% N, 21.84%; 1,4-dihydro-2-methyl-4-oxo-6-[(2-pyridinylethyl)amino]-5-pyrimidinecarbonitrile: mp 276°–278° C. (cryst. from methanol); IR (mineral oil) 3310, 2850, 2220, 1673 cm$^{-1}$; Anal. Calcd for $C_{13}H_{13}N_5O$: C, 61.16% H, 5.13% N, 27.43% and Found: C, 60.92% H, 5.15% N, 27.15%; 1,4-dihydro-2-methyl-4-oxo-6-[(4-pyridinylmethyl)amino]-5-pyrimidinecarbonitrile hydrochloride: mp>250° C. (cryst. from methanol-water); UV max (MeOH) 228 nm ($\epsilon$7110), 255 (8220), 225 (42790); Anal. Calcd for $C_{12}H_{11}N_5O.HCl$: C, 51.90% H, 4.35% N, 25.22% and Found: C, 51.82% H, 4.43% N, 25.36%; 1,4-dihydro-2-methyl-4-oxo-6-[(2-pyridinylmethyl)amino]-5-pyrimidinecarboitrile: mp>250° C. (cryst. from DMF-diethyl ether); NMR (DMSO-d$_6$) $\delta$ 215 (s, 3H), 4.68 (2H), 7.2 (2H), 7.7 (1H), 8.22 (1H), 8.47 (1H); Anal. Calcd for $C_{12}H_{11}N_5O$: C, 59.74% H, 4.60% N, 29.03% and Found: C, 59.69% H, 4.78% N, 28.83%; 1.4-dihydro-2-methyl-4-oxo-6-[(phenylmethyl)amino]-5-pyrimidinecarbonitrile: mp>290° C. (cryst. from DMF); NMR (DMSO-d$_6$) $\delta$ 8.3 (t, 1H), 7.25 (s, 5H), 4.57 (d, 2H), 2.2 (s, 3H); Anal. Calcd for $C_{13}H_{12}N_4O$: C, 64.98% H, 5.04% N, 23.32% and Found: C, 64.84% H, 5.27% N, 23.28%; 1,4-dihydro-6-[(2-furanylmethyl)amino]-2-methyl-4-oxo-5-pyrimidinecarbonitrile; mp 297°–300° C. (cryst. from methanol); NMR (DMSO-d$_6$) $\delta$ 2.2 (s, 3H), 4.55 (d, 2H), 6.25 (m, 2H), 7.5 (m, 1H), 8.2 (t, 1H), 11.4 (br, 1H); Anal. Calcd for $C_{11}H_{10}N_4O_2$: C, 57.38% H, 4.38% N, 24.34% and Found: C, 57.02% H, 4.49% N, 24.15%; 1,4-dihydro-2-methyl-6-[[2-(4-morpholinyl)ethyl]amino]-4-oxo-5-pyrimidinecarbonitrile: mp 227°–230° C. (cryst. from methanol-acetonitrile); NMR (CDCl$_3$) $\delta$ 2.4 (s, 3H), 2.5 (m, 6H), 3.65 (m, 6H), 3.35 (t, 1H); IR (mineral oil) 3340, 2850, 1670, 1595 cm$^{-1}$; Anal. Calcd for C$_{13}$H$_{18}$N$_4$O: C, 63.39% H, 7.36% N, 22.75% and Found: C, 63.56% H, 7.32% N, 22.64%; 1,4-dihydro-2-methyl-4-oxo-6-[[2-(3-thienyl)ethyl]amino]-5-pyrimidinecarbonitrile: mp 290°–292° C.; NMR (DMSO-d$_6$) δ 2.2 (s, 3H), 2.8 (t, 2H), 3.55 (m, 2H), 7.15 (m, 3H), 7.8 (t, 1H); Anal. Calcd for C$_{12}$H$_{12}$N$_4$OS: C, 55.36% H, 4.65% N, 21.52% and Found: C, 55.07% H, 4.61% N, 21.36%; 1,4-dihydro-6-[[2-(3,4-dimethoxyphenyl)ethyl]amino]-2-methyl-4-oxo-5-pyrimidinecarbonitrile: mp 238°–240° C. (cryst. from methanol); NMR (DMSO-d$_6$) δ 2.2 (s, 3H), 2.7 (t, 2H), 3.5 (m, 2H), 3.7 (s, 3H), 3.73 (s, 3H), 6.75 (m, 3H), 7.7 (t, 1H); Anal. Calcd for C$_{16}$H$_{18}$NO$_3$: C, 61.14% H, 5.77% N, 17.82% and Found: C, 60.63% H, 5.73% N, 17.68%; 1,4-dihydro-6-[[2-(1H-indol-3-yl)ethyl]amino]-2-methyl-4-oxo-5-pyrimidinecarbonitrile; mp 297°–300° C. (cryst. from methanol); NMR (DMSO-d$_6$) δ 2.2.(s, 3H), 2.9 (t, 2H), 3.6 (m, 2H), 7.1 (m, 4H), 7.85 (t, 1H), 10.75 (s, 1H), 11.5 (br, 1H); Anal. Calcd for C$_{16}$H$_{15}$N$_5$O: C, 65.51% H, 5.11% N, 23.88% and Found: C, 65.14% H, 5.21% N, 23.78%; 1,4-dihydro-2-methyl-4-oxo-6-[2-(3-pyridinyl)ethylamino]-5-pyrimidinecarbonitrile: mp>250° C. (cryst. from DMF); UV max (MeOH) 227 nm (ε38,300), 263 (8000), 269 (8000), 290 (6800); NMR (DMSO-d$_6$) δ 2.2 (s, 3H), 2.85 (t, 2H), 3.6 (m, 2H), 7.25 (m, 1H), 7.6 (m, 1H), 7.85 (br, 1H), 8.4 (m, 2H); Anal. Calcd for C$_{13}$H$_{13}$N$_5$O: C, 61.16% H, 5.13% N, 27.43% and Found: C, 60.62% H, 5.12% N, 27.36%; 1,4-dihydro-2-methyl-4-oxo-6-[2-(4-pyridinyl)ethylamino]-5-pyrimidinecarbonitrile: mp>250° C. (cryst. from DMF); UV max (MeOH) 226 nm (ε32,700), 257 (6370), 263 (6670), 289 (6870); NMR (DMSO-d$_6$) δ 2.2 (s, 3H), 2.82 (t, 2H), 3.6 (m, 2H), 7.18 (2d, 2H), 7.83 (br, 1H), 8.42 (2d, 2H), 11.5 (br, 1H): Anal. Calcd for C$_{13}$H$_{13}$N$_5$O: C, 61.15% H, 5.13% N, 27.43% and Found: C, 61.23% H, 5.20% N, 27.41%.

EXAMPLE 3

1,4-Dihydro-2-methyl-4-oxo-6-[(2-propenyl)amino]-5-pyrimidinecarbonitrile (I: R$^1$=Me, R$^2$=O, R$^3$=CN, R$^4$ to R$^8$=H, m=1, n=O, and R$^9$=ethenyl)

To a suspension of 2-cyano-3,3-bis(methylthio)-2-propenoic acid, methyl ester (8.12 g) in dimethoxyethane (13 mL) was added (2-propenyl)amine (2.51 g). The mixture dissolved. After about 15 min the solvent was evaporated under nitrogen and the solid residue was filtered with diethyl ether to give 2-cyano-3-methylthio-3-(2-propenyl)amino-2-propenoic acid, methyl ester (8.61 g).

Similarly, but replacing (2-propenyl)amine with 3-aminopyridine, the following compound of formula VI was obtained; 2-cyano-3-methylthio-3-(3-pyridinyl)amino-2-propenoic acid, methyl ester: mp 93°–94° C.

To a suspension of acetamidine hydrochloride (1.25 g, 1.1 eq) in DMF (45 mL) was added 2-cyano-3-methylthio-3-(2-propenyl)amino-2-propenoic acid, methyl ester (12.54 g, 1 eq) and potassium carbonate (1.82 g, 2.2 eq). The mixture was heated to 130° C. for 22 hr, cooled in an ice water bath and diluted with water (20 mL). The precipitate was collected (0.7 g). The filtrate was evaporated and suspended in a small amount of water (7 mL) and filtered to give more product (0.3 g). The product was crystallized from DMF to yield the title compound (0.44 g): mp>260° C.; UV max (MeOH) 289 nm (ε6610), 269 (5640), 227 (42640); NMR (DMSO-d$_6$) δ 2.2 (s, 3H), 3.95 (m, 2H), 5.05 (m, 2H), 5.8 (m, 1H), 7.9 (t, 1H); Anal. Calcd for C$_9$H$_{10}$N$_4$O: C, 56.84% H, 5.26% N, 29.47% and Found: C, 56.58% H, 5.34% N, 29.56%.

Similarly, replacement of 2-cyano-3-methylthio-3-(2-propenyl)amino-2-propenoic acid, methyl ester with 2-cyano-3-methylthio-3-(3-pyridinyl)amino-2-propenoic acid, methyl ester, the following compound of formula I was obtained: 1,4-dihydro-2-methyl-4-oxo-6-[(3-pyridinyl)amino]-5-pyrimidinecarbonitrile: mp>260° C. (cryst. from DMF); IR (mineral oil) 3320, 2700, 2210, 1695 cm$^{-1}$; NMR (DMSO-d$_6$) δ 2.2 (s, 3H), 7.9 (m, 4H), 9.75 (br, 2H); Anal. Calcd for C$_{11}$H$_9$N$_5$O: C, 58.09% H, 3.99% N, 30.82% and Found: C, 57.80% H, 4.18% N, 30.36%.

EXAMPLE 4

4-Amino-2-methyl-6-[(3-pyridinylmethyl)amino]-5-pyrimidinecarbonitrile (I: R$^1$=Me, R$^2$=NH, R$^3$=CN, R$^4$ to R$^8$=H, m=1, n=O and R$^9$=3-pyridinyl)

To phosphorous oxychloride (42.9 g, or 26.1 mL, 8 eq) preheated to 100° C. (bath temp.) was added, the sodium salt of 1,4-dihydro-2-methyl-4-oxo-6-[(3-pyridinylmethyl)amino]-5-pyrimidinecarbonitrile (described in Example 2), (9.2 g, 1 eq). The reaction mixture was heated for 2 hr. The solution was cooled and poured into ice water (900 mL) with stirring. The resulting solution was basified with sodium hydroxide (50%, 100 mL). Some ethyl acetate was added, and the resulting precipitate was filtered and dried to yield a solid (4.7 g). The aqueous filtrate was extracted with ethyl acetate, and the extract was dried and evaporated to give a residue (1.8 g). The combined material was crystallized from chloroform-hexane to give 4-chloro-2-methyl-6-[(3-pyridinylmethyl)amino]-5-pyrimidinecarbonitrile: mp 165°–167° C.; UV max (MeOH) 305 nm (ε4130), 254 (18100).

A solution of the latter compound (1.5 g, 1 eq) in methanol (25 mL) was cooled in an ice bath. Ammonia was passed into the solution for 20 min. The reaction mixture turned yellow. The mixture was heated in a closed container to 60° C. for 2 hr. The precipitate began to appear concomitantly with discoloration. The mixture was stirred at room temperature overnight. The solvent was removed, water was added, and the solid was filtered to give crude product (1.4 g). Three crystallizations from DMF yielded the title compound (0.3 g): mp>280° C.; UV max (MeOH) 254 nm (ε12740), 234 (44070); Anal. Calcd for C$_{12}$H$_{12}$N$_6$: C, 59.98% H, 5.04% N, 34.98% and Found: C, 59.50% H, 5.13% N, 34.41%.

EXAMPLE 5

1,4-Dihydro-2-methyl-6-[(3-pyridinylmethyl)amino]-4-thioxo-5-pyrimidinecarbonitrile (I: R$^1$=Me, R$^2$=S, R$^3$=CN, R$^4$ to R$^8$=H, m=1, n=O, and R$^9$=3-pyridinyl)

To ethanol (5 mL) was added a solution of potassium hydroxide (1.5 mL, 4 molar in water-ethanol 1:9). The mixture was cooled in ice-bath. Hydrogen sulphide was passed through the solution for 15 min. 4-Chloro-2-methyl-6-[(3-pyridinylmethyl)amino]-5-pyrimidinecarbonitrile (described in Example 4, 0.78 g, 1 eq) in ethanol (7 mL) was added to the solution. The mixture was stirred at room temperature for 2.5 hr. Another portion of potassium hydroxide solution (1.5 mL) in ethanol (3.5 mL) was added. Hydrogen sulfide passed through for 15 min. It was stirred overnight at room temperature. The mixture was filtered and the precipitate was washed with some ethanol, to yield crude product (0.7 g). The solid was crystallized twice from DMF to yield the title compound (0.25 g): mp 310°–312° C.; NMR (DMSO-d$_6$)δ 13.2 (br, 1H), 8.8 (br, 1H), 8.5 (m, 2H), 7.5 (m, 2H), 4.6 (d, 2H), 2.3 (s, 3H); Anal. Calcd for C$_{12}$H$_{11}$N$_5$S: C, 56.01% H, 4.31% N, 27.22% and Found: C, 55.48%, H, 4.49% N, 26.68%.

EXAMPLE 6

1,4-Dihydro-2-methyl-4-oxo-6-[(3-pyridinylmethyl)amino]-5-pyrimidinecarboxamide (I: R$^1$=Me, R$^2$=O, R$^3$=aminocarbonyl, R$^4$ to R$^8$=H, m=1, n=O, and R$^9$=3-pyridinyl)

Sulfuric acid (4 mL) was added to 1,4-dihydro-2-methyl-4-oxo-6-[(3-pyridinylmethyl)amino]-5-pyrimidinecarbonitrile (1.2 g, described in Example 2). The mixture was heated to 70° C. for 4 hr. The reaction was cooled to room temperature, and carefully poured on crushed ice (75 mL). The resulting solution was neutralized with sodium hydroxide (50%, aqueous, 12.5 mL) when precipitate appeared. Filtrate after removal of precipitate showed the pH to be 4.5–5.0. Eight more drops of sodium hydroxide were added. More precipitate appeared. This was filtered off. The pH was checked and found to be 5. One more drop changed the pH to 8. The combined solid was dried and crystallized from boiling DMF to yield the title compound (1.1 g): mp 264°–266°; Anal. Calcd for C$_{12}$H$_{14}$N$_5$O$_2$: C, 55.38% H, 5.38% N, 26.9% and Found: C, 55.26% H, 5.12% N, 26.70%; IR (mineral oil) 3760, 3000, 1645, 1585 cm$^{-1}$; NMR (DMSO-d$_6$) δ 8.5 (1H, m), 7.55 (1H, m), 7.25 (1H, m), 9.15 (1H, m), 4.7 (2H, d), 2.22 (3H, s).

EXAMPLE 7

2-Methylpropanimidamide (II: R$^1$=1-methylethyl)

Anhydrous hydrogen chloride was passed into a solution of 2-methylpropanenitrile (30.4 g, 40 mL) in anhydrous ethanol (25 mL) until saturation at 25° C. The stoppered reaction mixture did not crystallize after 3 days and was evaporated to dryness under reduced pressure. The oily residue crystallized after a while and was treated with a 10% solution of anhydrous ammonia in ethanol (130 mL). After stirring for 3 hr, ammonium chloride was filtered off, and the filtrate was concentrated until crystalline. The first batch of the product (24.7 g) was collected by filtration, the second batch (9.6 g) was obtained on further concentration of the filtrate to give a total yield of the hydrochloride salt of the title compound (34.3 g): mp 155°–157° C.

Similarly, by replacing 2-methylpropanenitrile with propanenitrile, 2,2-dimethylpropanenitrile, cyclopropylnitrile, or 2-phenylethanenitrile, the following compounds of formula II were obtained respectively: propanimidamide hydrochloride (mp 130°–132° C.), 2,2-dimethylpropanimidamide hydrochloride (mp 186°–188° C.), cyclopropylmethanimidamide hydrochloride (mp 123°–125° C.), and 2-phenylethanimidamide hydrochloride (mp 145°–147° C.).

EXAMPLE 8

1,4-Dihydro-2-(1-methylethyl)-6-(methylthio)-4-oxo-5-pyrimidinecarbonitrile (IV: R$^1$=1-methylethyl)

A solution of 2-methylpropanimidamide hydrochloride (7.0 g, described in Example 7) in dimethylformamide (15 mL) was added dropwise to a suspension of sodium hydride (3.0 g, 50% in mineral oil, prewashed with hexane) in dimethylformamide (15 mL) and the whole mixture was left at 25° C. for 1 hr. 2-Cyano-3,3-bis(methylthio)-2-propenoic acid, methyl ester (6.5 g) in dimethylformamide (15 mL) was then added dropwise, and the reaction mixture was stirred for an additional 4 hr at 25° C. Water (25 mL) was then added, and acidification with concentrated hydrochloric acid (10 mL) precipitated the product. The precipitate was collected and air dried to give the title compound (6.0 g): mp>260° C.

Similarly, by replacing 2-methylpropanimidamide with another 20 compound of formula described in Example 7, the following compounds of formula IV were obtained respectively: 1,4-dihydro-2-ethyl-6-(methylthio)-4-oxo-5-pyrimidinecarbonitrile (mp>260° C.), 1,4-dihydro-2-(1,1-dimethylethyl)-6-(methylthio)-4-oxo-5-pyrimidinecarbonitrile (mp>360° C.), 2-cyclopropyl-1,4-dihydro-6-(methylthio)-4-oxo-5-pyrimidinecarbonitrile [NMR (DMSO-d$_6$) δ 1.2 (d, 4H), 2.0 (m, 1H), 2.5 (s, 3H)], and 1,4-dihydro-6-(methylthio)-4-oxo-2-(phenylmethyl)-5-pyrimidinecarbonitrile [NMR (DMSO-d$_6$) δ 2.6 (s, 3H), 4.0 (s, 2H), 7.4 (s, 5H)].

EXAMPLE 9

1,4-Dihydro-2-(1-methylethyl)-4-oxo-6-[(3-pyridinylmethyl)amino]-5-pyrimidinecarbonitrile (I: R$^1$=1-methylethyl, R$^2$=O, R$^3$=CN, R$^4$ to R$^8$=H, m=1, n=O, and R$^9$=3-pyridinyl)

3-(Aminomethyl)pyridine (16 mL) was added to 1,4-dihydro-2-(1-methylethyl)-6-(methylthio)-4-oxo-5-pyrimidinecarbonitrile (6 g, described in Example 8) in 1,2-dimethoxyethane (50 mL), and the mixture was refluxed overnight. Evaporation to dryness under reduced pressure gave the crude product which was chromatographed over silica acid with chloroform-methanol (97:3). The product was isolated as a colorless solid which was crystallized from methanol-water to give the title compound (3.4 g): mp>260° C.; NMR (DMSO-d$_6$) δ 1.1 (d, 6H), 2.7 (m, 1H), 4.55 (m, 2H), 7.3–8.4 (m, 4H), 11.5 (br, 2H); IR (mineral oil) 3335, 2900, 2210, 1660, 1585 cm$^{-1}$; Anal. Calcd for C$_{14}$H$_{15}$N$_5$O: C, 62.44% H, 5.61% N, 25.94% and Found: C, 62.12% H, 5.63% N, 25.92%.

Similarly, by replacing 1,4-dihydro-2-(1-methylethyl)-6-(methylthio)-4-oxo-5-pyrimidinecarbonitrile with another compound of formula IV described in Example 8, the following compounds of formula I were obtained respectively: 1,4-dihydro-2-ethyl-4-oxo-6-[(3-pyridinylmethyl)amino]-5-pyrimidinecarbonitrile hydrochloride: mp>265° C. (cryst. from methanol-water); NMR (DMSO-d$_6$) δ 1.05 (t, 3H), 2.45 (d, 2H), 4.75 (d, 2H), 6.2 (br, 2H), 8.4 (m, 4H), 11.4 (br, 1H); IR (mineral oil) 3280, 2600, 2220, 2080, 1960, 1650 cm$^{-1}$; Anal. Calcd for C$_{13}$H$_{14}$ClN$_3$O: C, 53.52% H, 4.84% N, 24.00% and Found: C, 53.17% H, 4.84% N, 23.74%; 1.4-dihydro-2-(1,1-dimethylethyl)-4-oxo-6-[(3-pyridinylmethyl)amino]-5-pyrimidinecarbonitrile hydrochloride: mp>260° C. (cryst. from methanol-water); NMR (DMSO-d$_6$) δ 1.17 (s, 9H), 4.15 (d, 2H), 8.5 (m, 4H), 8.6 (br, 1H), 8.9 (br, 1H), 11.9 (s, 1H); IR (mineral oil) 3280, 3180, 3100, 2600, 2220, 2100, 1970, 1660 cm$^{-1}$; Anal. Calcd for C$_{18}$H$_{17}$N$_5$O: C, 56.34% H, 5.67% N, 21.90% and Found: C, 57.74% H, 5.61% N, 21.96%; 2-cyclopropyl-1,4-dihydro-4-oxo-6-[(3-pyridinylmethyl)amino]-5-pyrimidinecarbonitrile: mp>260° C. (cryst. from 1,2-dimethoxyethane); NMR (DMSO-d$_6$) δ 1.0 (m, 4H), 1.8 (m, 1H), 4.5 (d, 2H), 7.5–8.5 (m, 4H), 12.4 (br, 1H); IR (mineral oil 3300, 2850, 2190, 1685 cm$^{-1}$; Anal. Calcd for $C_{14}H_{13}N_5O$: C, 62.91% H, 4.90% N, 26.20% and Found: C, 62.31% H, 4.90% N, 25.98%; and 1,4-dihydro-4-oxo-2-(phenylmethyl)-6-[(3-pyridinylmethyl)amino]-5-pyrimidinecarbonitrile: mp>260° C. (cryst. from acetonitrile); NMR (DMSO-d$_6$) δ 3.8 (s, 2H), 4.5 (d, 2H), 7.25 (s, 5H), 7.45 and 8.4 (m, 4H), 8.4 (br, 1H); IR (mineral oil) 3330, 2800, 2210, 1660, 1590 cm$^{-1}$; Anal. Calcd for $C_{18}H_{15}N_5O$: C, 68.13% H, 4.76%, N, 22.07% and Found: C, 67.83% H, 4.82% N, 21.85%.

EXAMPLE 10

Test for Cardiotonic Activity in Isolated Cat Papillary Muscle

A cat of either sex was anesthetized with Na pentobarbital, 25–30 mg/kg i.v. The heart was rapidly removed and placed in cool Tyrode's solution which had been equilibrated with 95% $O_2$-5% $CO_2$. The right ventricle was opened by cutting down the sides and around the apex so that the free wall could be folded back on the atriventricular groove. Usually at least three suitably-sized papillary muscles were found (1 mm or less in thickness). Threads were tied around the chordae tendonae and the base of the muscle just above its point of insertion into the ventricular wall. The chordae were cut, and the muscle was removed along with a small button of ventricular wall. If a sufficient number of papillary muscles were not present, trabeculae carnae could also be used. The best ones were usually found inserting just under the valve.

The preparations were mounted in tissue baths containing Tyrode's solution at 37° C. bubbled with 95% $O_2$-5% $CO_2$. One thread was affixed to a tissue holder incorporating a pair of platinum electrodes and the other thread was attached to a force displacement transducer. Initial tension placed on the preparation was 0.2 g (less for very small muscles). The preparations were stimulated with square-wave pulses, 2–4 msec. in duration and 10% above threshold voltage, at a rate of 0.5 Hz. The muscles were then gently and gradually stretched to their optimum force-length relation (at which twitch tension was maximal-further stretching did not result in any further increase in the overall magnitude of the twitch). The preparations were then allowed to equilibrate for one hour with frequent changes of the bathing fluid (10–15 min intervals). The test compound was added to the bath in 0.1 mL of vehicle and incubated with the preparation for 15 min or until peak effect was attained.

Using this method, the following representative compounds of formula I were effective for increasing the force of contraction of the papillary muscle (the amount of test compound in the bath and increase in contractility is given in the parenthesis): 1,4-dihydro-2-methyl-4-oxo-6-[(3-pyridinylmethyl)amino]-5-pyrimidinecarbonitrile (at 10$^{-4}$ molar increased contractility by 98%), 1,4-dihydro-2-methyl-4-oxo-6-[(4-pyridinylmethyl)amino]-5-pyrimidinecarbonitrile (at 10$^{-4}$ molar increased contractility by 139%), 1,4-dihydro-2-methyl-4-oxo-6-[(phenylethyl)amino]-5-pyrimidinecarbonitrile (at 10$^{-4}$ molar increased contractility by 142%), 1,4-dihydro-2-ethyl-4-oxo-6-[(3-pyridinylmethyl)amino]-5-pyrimidinecarbonitrile (at 10$^{-4}$ molar increased contractility by 140%), 1,4-dihydro-6-[(2-furanylmethyl)amino]-2-methyl-4-oxo-5-pyrimidinecarbonitrile (at 10$^{-4}$ molar increased contractility by 108%, 2-cyclopropyl-1,4-dihydro-4-oxo-6-[(3-pyridinylmethyl)amino]-5-pyrimidinecarbonitrile (at 10$^{-4}$ molar increased contractility by 129%), 1,4-dihydro-2-methyl-6-[[2-(4-morpholinyl)ethyl]amino]-4-oxo-5-pyrimidinecarbonitrile (at 10$^{-4}$ molar increased contractility by 62%), 1,4-dihydro-2-methyl-4-oxo-6-[[2-(3-thienyl)ethyl]amino]-5-pyrimidinecarbonitrile (at 10$^{-4}$ molar increased contractility by 149%), and 1,4-dihydro-2-methyl-4-oxo-6-[(2-propenyl)amino]-5-pyrimidinecarbonitrile (at 10$^{-4}$ molar increased contractility by 61%).

EXAMPLE 11

Pentobarbital-induced Cardiac Failure in the Dog

A dog of either sex was anesthetized with Na pentobarbital, 30–35 mg/kg i.v. The trachea was intubated and the animal was respired at a rate of 20 breaths/min (stroke volume=15 cc/kg). Both femoral veins were cannulated. One cannula was used for infusion of pentobarbital to induce and maintain failure, the other for injection of test compounds. A cannual was inserted into the aorta via a femoral artery and the cannula was attached to a blood pressure transducer for measurement of systolic, diastolic and mean aortic blood pressure. A Millar pressure-tip catheter was inserted into the other femoral artery and advanced into the left ventricle to record intraventricular pressure and dP/dt. Subdermal needle electrodes were used to record a lead II electrocardiogram and heart rate.

Following a stabilization period of at least 30 min, experimental failure was induced by the i.v. infusion of Na pentobarbital, 0.75 mg/kg/min in 0.2 mL of saline/min, until a 40–50% decrease in peak positive dP/dt was obtained. The failure state was maintained at this level throughout the experiment by continuous infusion of Na pentobarbital, 0.11–0.15 mg/kg/min. Once the maintenance infusion was started, at least 15 min were allowed to elapse before test drugs were administered.

Test compounds were prepared in N saline. Increasingly higher doses were given i.v. at 30 min-1 hr intervals in order to determine a therapeutic (50% increase in dP/dt) to toxic (appearance of arrhythmias) ratio where possible.

Using this method, the following representative compounds of formula I were effective for increasing the cardiac contractility of the heart (the amount of test compound in mg per kg of body weight administered i.v. to give a 50% increase in dP/dt is given in the parenthesis): 1,4-dihydro-2-methyl-4-oxo-6-[(3-pyridinylmethyl)amino]-5-pyrimidinecarbonitrile (0.06 mg/kg), 1,4-dihydro-2-methyl-4-oxo-6-[(4-pyridinylmethyl)amino]-5-pyrimidinecarbonitrile (0.07 mg/kg), 1,4-dihydro-2-ethyl-4-oxo-6-[(3-pyridinylmethyl)amino]-5-pyrimidinecarbonitrile (0.05 mg/kg), 1,4-dihydro-6-[(2-furanylmethyl)amino]-2-methyl-4-oxo-5-pyrimidinecarbonitrile (0.06 mg/kg), 2-cyclopropyl-1,4-dihydro-4-oxo-6-[(3-pyridinylmethyl)amino]-5-pyrimidinecarbonitrile (0.02 mg/kg), and 1,4-dihydro-2-methyl-4-oxo-6-[[2-(3-thienyl)ethyl]amino]-5-pyrimidinecarbonitrile (0.08 mg/kg).

We claim:

1. A compound of the formula

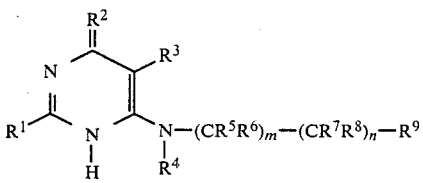

in which R¹ is lower alkyl, cyclo(lower)alkyl, phenyl(lower)alkyl, or trifluoromethyl; R² is oxo, thioxo or imino; R³ is cyano, aminocarbonyl, nitro, methylsulfonyl or aminosulfonyl; R⁴, R⁵, R⁶, R⁷ and R⁸ each independently is hydrogen or lower alkyl; R⁹ is lower alkenyl, 1-piperidinyl, 1-pyrrolidinyl, 1-piperazinyl, lower alkynyl, cyclo(lower)alkyl, 2, 3 or 4-pyridinyl, 2 or 3-furanyl, 2 or 3-indolyl, 2 or 3-thienyl, 5-imidazolyl, 4-morpholinyl, phenyl, phenyl mono- or disubstituted with hydroxy or lower alkoxy, imidazolyl, 4-thiomorpholinyl, pyrazinyl, pyridazinyl, triazinyl, pyrrolyl, pyrazolyl, thiazolyl, oxadiazolyl, thiadiazolyl, isoxazolyl, oxathiazolyl, quinolinyl, isoquinolinyl, pyridopyrimidinyl, benzoxazolyl, benzimidazolyl, benzthiazolyl, benzoxazinyl, benzpyronyl, or isoindolyl, and m and n each independently is an integer 0 to 2; or a therapeutically acceptable addition salt thereof.

2. A compound of claim 1 wherein R¹ is lower alkyl, cyclo(lower)-alkyl or benzyl; R² is oxo, thioxo or imino; R³ is cyano or aminocarbonyl; R⁴, R⁶ and R⁸ each independently is hydrogen or lower alkyl; R⁵ and R⁷ are hydrogen; R⁹ is lower alkenyl, cyclo(lower)alkyl, 2, 3 or 4-pyridinyl, 2 or 3-furanyl, 2 or 3-indolyl, 2 or 3-thienyl, 4-morpholinyl, phenyl or phenyl mono- or disubstituted with hydroxy or lower alkoxy; and m and n each independently is an integer 0 to 2; or a therapeutically acceptable addition salt thereof.

3. A compound of claim 1 wherein R¹ is lower alkyl, cyclo(lower)alkyl or benzyl; R² is oxo or thioxo, R³ is cyano; R⁴, R⁵ and R⁷ are hydrogen; R⁶ and R⁸ each independently is hydrogen or lower alkyl; R⁹ is lower alkenyl, 2, 3 or 4-pyridinyl, 2-furanyl, 3-indolyl, 3-thienyl, 4-morpholinyl, phenyl or phenyl mono- or disubstituted with lower alkoxy; and m and n each independently is the integer 0 or 1; or a therapeutically acceptable addition salt thereof.

4. 1,4-Dihydro-2-methyl-4-oxo-6-[(3-pyridinylmethyl)amino]-5-pyrimidinecarbonitrile, a compound of claim 1.

5. 1,4-Dihydro-2-methyl-6-[N-methyl-N-(3-pyridinylmethyl)amino]-4-oxo-5-pyrimidinecarbonitrile, a compound of claim 1.

6. 1,4-Dihydro-2-methyl-4-oxo-6-[(phenylethyl)amino]-5-pyrimidinecarbonitrile, a compound of claim 1.

7. 1,4-Dihydro-2-methyl-4-oxo-6-[(2-pyridinylethyl)amino]-5-pyrimidinecarbonitrile, a compound of claim 1.

8. 1,4-Dihydro-2-methyl-4-oxo-6-[(4-pyridinylethyl)amino]-5-pyrimidinecarbonitrile, a compound of claim 1.

9. 1,4-Dihydro-2-methyl-4-oxo-6-[(2-pyridinylmethyl)amino]-5-pyrimidinecarbonitrile, a compound of claim 1.

10. 1,4-Dihydro-2-methyl-4-oxo-6-[(phenylmethyl)amino]-5-pyrimidinecarbonitrile, a compound of claim 1.

11. 1,4-Dihydro-6-[(2-furanylmethyl)amino]-2-methyl-4-oxo-5-pyrimidinecarbonitrile, a compound of claim 1.

12. 1,4-Dihydro-2-methyl-6-[[2-(4-morpholinyl)ethyl]amino]-4-oxo-5-pyrimidinecarbonitrile, a compound of claim 1.

13. 6-[(Cyclohexylmethyl)amino]-1,4-dihydro-2-methyl-4-oxo-5-pyrimidinecarbonitrile, a compound of claim 1.

14. 1,4-Dihydro-2-methyl-4-oxo-6-[[2-(3-thienyl)ethyl]amino]-5-pyrimidinecarbonitrile, a compound of claim 1.

15. 1,4-Dihydro-6-[[2-(3,4-dimethoxyphenyl)ethyl]amino]-2-methyl-4-oxo-5-pyrimidinecarbonitrile, a compound of claim 1.

16. 1,4-Dihydro-6-[[2-(1H-indol-3-yl)ethyl]amino]-2-methyl-4-oxo-5-pyrimidinecarbonitrile, a compound of claim 1.

17. 1,4-Dihydro-2-methyl-4-oxo-6-[2-(3-pyridinyl)ethylamino]-5-pyrimidinecarbonitrile, a compound of claim 1.

18. 1,4-Dihydro-2-methyl-4-oxo-6-[2-(4-pyridinyl)ethylamino]-5-pyrimidinecarbonitrile, a compound of claim 1.

19. 1,4-Dihydro-2-methyl-4-oxo-6-[(2-propenyl)amino]-5-pyrimidinecarbonitrile, a compound of claim 1.

20. 1,4-Dihydro-2-methyl-4-oxo-6-[(3-pyridinyl)amino]-5-pyrimidinecarbonitrile, a compound of claim 1.

21. 4-Amino-2-methyl-6-[(3-pyridinylmethyl)amino]-5-pyrimidinecarbonitrile, a compound of claim 1.

22. 1,4-Dihydro-2-methyl-6-[(3-pyridinylmethyl)amino]-4-thioxo-5-pyrimidinecarbonitrile, a compound of claim 1.

23. 1,4-Dihydro-2-methyl-4-oxo-6-[(3-pyridinylmethyl)amino]-5-pyrimidinecarboxamide, a compound of claim 1.

24. 1,4-Dihydro-2-ethyl-4-oxo-6-[(3-pyridinylmethyl)amino]-5-pyrimidinecarbonitrile, a compound of claim 1.

25. 1,4-Dihydro-2-(1-methylethyl)-4-oxo-6-[(3-pyridinylmethyl)amino]-5-pyrimidinecarbonitrile, a compound of claim 1.

26. 2-Cyclopropyl-1,4-dihydro-4-oxo-6-[(3-pyridinylmethyl)amino]-5-pyrimidinecarbonitrile, a compound of claim 1.

27. 1,4-Dihydro-2-(1,1-dimethylethyl)-4-oxo-6-[(3-pyridinylmethyl)amino]-5-pyrimidinecarbonitrile, a compound of claim 1.

28. 1,4-Dihydro-4-oxo-2-phenylmethyl-6-[(3-pyridinylmethyl)amino]-5-pyrimidinecarbonitrile, a compound of claim 1.

29. 1,4-Dihydro-2-methyl-4-oxo-6-[[1-(3-pyridinyl)ethyl]amino]-5-pyrimidinecarbonitrile, a compound of claim 1.

30. A method of increasing cardiac contractility in a mammal, which comprises administering to the mammal in need thereof an effective cardiotonic amount of a compound of claim 1.

31. A cardiotonic pharmaceutical composition, which comprises a compound of claim 1 and a pharmaceutically acceptable carrier therefor.

32. A cardiotonic pharmaceutical composition, which comprises a compound of claim 1 and an agent commonly used in treatment of congestive heart failure.

33. The cardiotonic pharmaceutical composition of claim 32 wherein said agent is selected from isosorbide dinitrate, captopril, nifedipine, hydralazine, prazosin, hydrochlorothiazide, furosemide, spironolactone, digitalis and dobutamine.

* * * * *